United States Patent [19]
Van Erp

[11] Patent Number: 5,690,645
[45] Date of Patent: Nov. 25, 1997

[54] DEVICE FOR MOVING A CATHETER IN A CONTROLLED MANNER

[75] Inventor: Wilhelmus Petrus Martinus Maria Van Erp, Leek, Netherlands

[73] Assignee: Cordis Corporation, Miami, Fla.

[21] Appl. No.: 671,126

[22] Filed: Jun. 19, 1996

[30] Foreign Application Priority Data

Jun. 28, 1995 [NL] Netherlands ............................ 1000685

[51] Int. Cl.⁶ .................................................. A61F 11/00
[52] U.S. Cl. ........................... 606/108; 604/116; 604/117; 604/178
[58] Field of Search ................................... 604/116, 117, 604/159, 178; 606/107, 108, 205

[56] References Cited

U.S. PATENT DOCUMENTS

| | | | |
|---|---|---|---|
| 3,452,740 | 7/1969 | Muller | 606/108 X |
| 4,484,911 | 11/1984 | Berlin et al. | 606/108 X |
| 4,889,118 | 12/1989 | Schwiegerling | 606/108 |
| 4,955,890 | 9/1990 | Yamamoto et al. | 606/108 |
| 5,131,379 | 7/1992 | Sewell, Jr. | 606/108 X |
| 5,163,941 | 11/1992 | Garth et al. | 606/108 |
| 5,290,310 | 3/1994 | Makower et al. | 606/108 X |
| 5,409,478 | 4/1995 | Gerry et al. | 606/108 X |
| 5,601,568 | 2/1997 | Chevillon et al. | 606/108 |

*Primary Examiner*—Sam Rimell
*Assistant Examiner*—Robert V. Racunas
*Attorney, Agent, or Firm*—Paul A. Coletti

[57] ABSTRACT

The invention relates to a device for moving a catheter in a controlled manner. The device has a frame, guiding member attached to the frame for the purpose of guiding the catheter, a first engaging mechanism in order to manually engage the guiding means, second engaging means for the purpose of engaging the catheter guided by the guiding machines, wherein the first and second engaged mechanism are connected in such a manner that, on moving the first engaging mechanism, the catheter is moved in relation to the frame. Furthermore, a signalling device is attached to the engaged mechanism for the purpose of giving off a signal corresponding to the displacement of the catheter.

9 Claims, 4 Drawing Sheets

DEVICE FOR MOVING A CATHETER IN A CONTROLLED MANNER

FIELD OF THE INVENTION

The invention relates to a device used to move a catheter in a controlled manner. Such a device is for instance used for the purpose of withdrawing a catheter, provided with an ultrasonic probe, in a controlled manner from the body of a patient Each time the catheter is pulled back over a certain, predetermined distance, a recording is made using an ultrasonic imaging system. Thus a series of images an be obtained, which can give the physician carrying out the procedure the required information on the condition of the tissue of a patient. With the known device, a step motor is used which is activated by digital control means. Each time the step motor has been rotated a number of predetermined steps, the digital control means will signal that a recording is to be made.

SUMMARY OF THE INVENTION

Known devices for moving a catheter in a controlled manner is expensive, bulky, heavy and rather awkward to use.

So, the object of the invention is to provide a device of the type described herein, which is easy to use and nevertheless capable of moving a catheter, with the required degree of accuracy, in a controlled manner.

This object is achieved with the device for moving a catheter in a controlled manner, comprising: a frame; guiding means arranged to the frame for the purpose of guiding a catheter; first engaging means in order to manually engage the guiding means; second engaging means for the purpose of engaging the catheter guided by said guiding means; wherein the first and second engaging means are connected in such a manner that, on moving the first engaging means, the catheter is moved in relation to the frame; and signaling means engaged by said engaging means for the purpose of giving off a signal corresponding to the displacement of the catheter. By manually moving the first engaging means, the second engaging means, which engages the catheter and moves it along, is activated. The signal corresponding to the displacement of the catheter is generated by the device itself, so that a simple, easy to handle and reliable action is achieved.

The second engaging means can for instance be moved in a suitable manner by being compressed and released manually.

Each time the manually operated engaging means is moved one stroke, the contacts at the end of the stroke will engage and a signal will be given off. As a result a very simple and stepwise displacement of the catheter in conjunction with a directly corresponding stepwise signal.

In a suitable manner, the size of the stroke can be defined by suitably adjusting the stop device. When one is interested in a small area, the stroke can be set at a small value, and when a more general impression is required, a large stroke can be selected.

A very simple operation of the device according to the invention can be achieved with the engaging means compressed for instance, for the purpose of moving the catheter; the engaging means may then be released in order to return to the initial position after which a subsequent displacement stroke may be carried out.

Inside the guiding means the catheter is surrounded by an o-ring, so that proper engagement of the friction means, formed by this o-ring, is effected.

By temporarily fixing the device by means of fixing agents to the skin of the patient, an accurate point of reference of the device in relation to the patent, and consequently an accurate reference of the catheter movements in relation to the patient, is achieved.

DESCRIPTION OF THE DRAWINGS

The invention will be explained in greater detail in the following description with reference to the attached drawings.

DETAILED DESCRIPTION OF THE INVENTION

Figure 1:
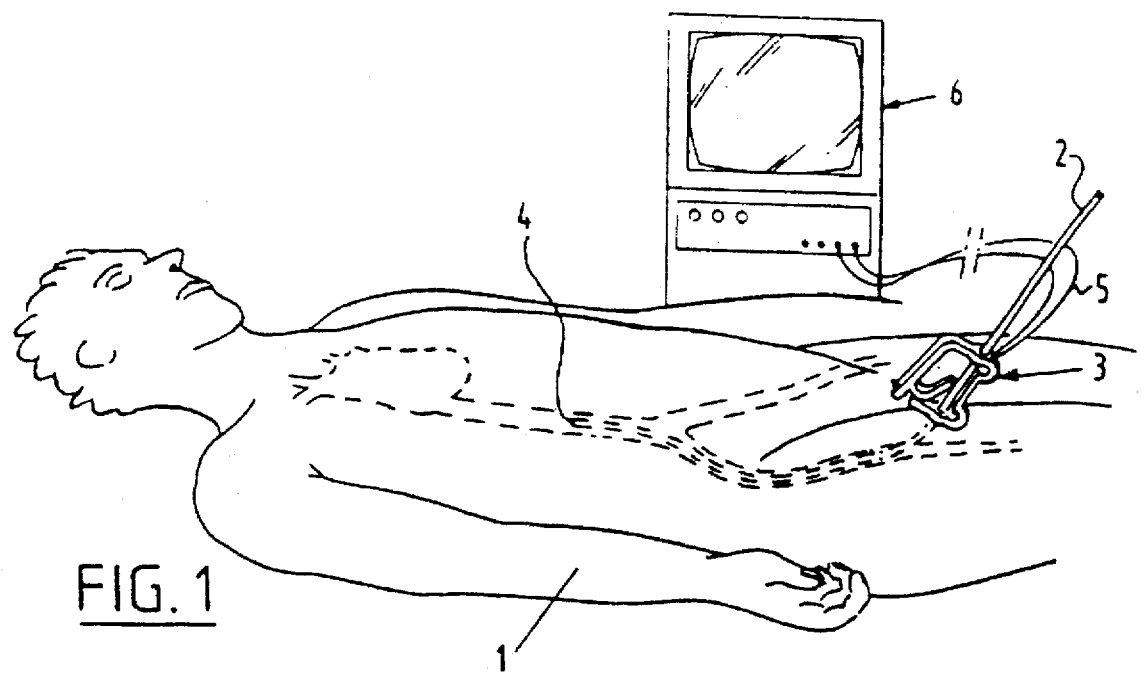
FIG. 1 shows a perspective view of the use of the device according to the invention.

FIG. 1 shows a patient 1 into whom a catheter 2 has been introduced. The catheter 2 has been guided through a device 3 according to the invention, with which the catheter 2 can be withdrawn, from the body of the patient 1 in a controlled manner.

The catheter 2 may be of a type which has been provided with an ultrasonic tip 4. By means of the signal emitted by the ultrasonic tip 4 an image of the inside of the patient can be formed via a receiver not illustrated in FIG. 1, by means of the imaging device 6. By means of a signal line 5, which is connected to signalling means of the device 3 to be described in greater detail below, a signal can be conveyed to the imaging device 6 which corresponds to the movement of the catheter 2, and hence the ultrasonic tip 4, effected by the device 3. By means of the signal conveyed via the signal line 5, a relation can be established between the relative longitudinal position of the catheter tip 4 and the image formed by the imaging device 6.

Figure 2:
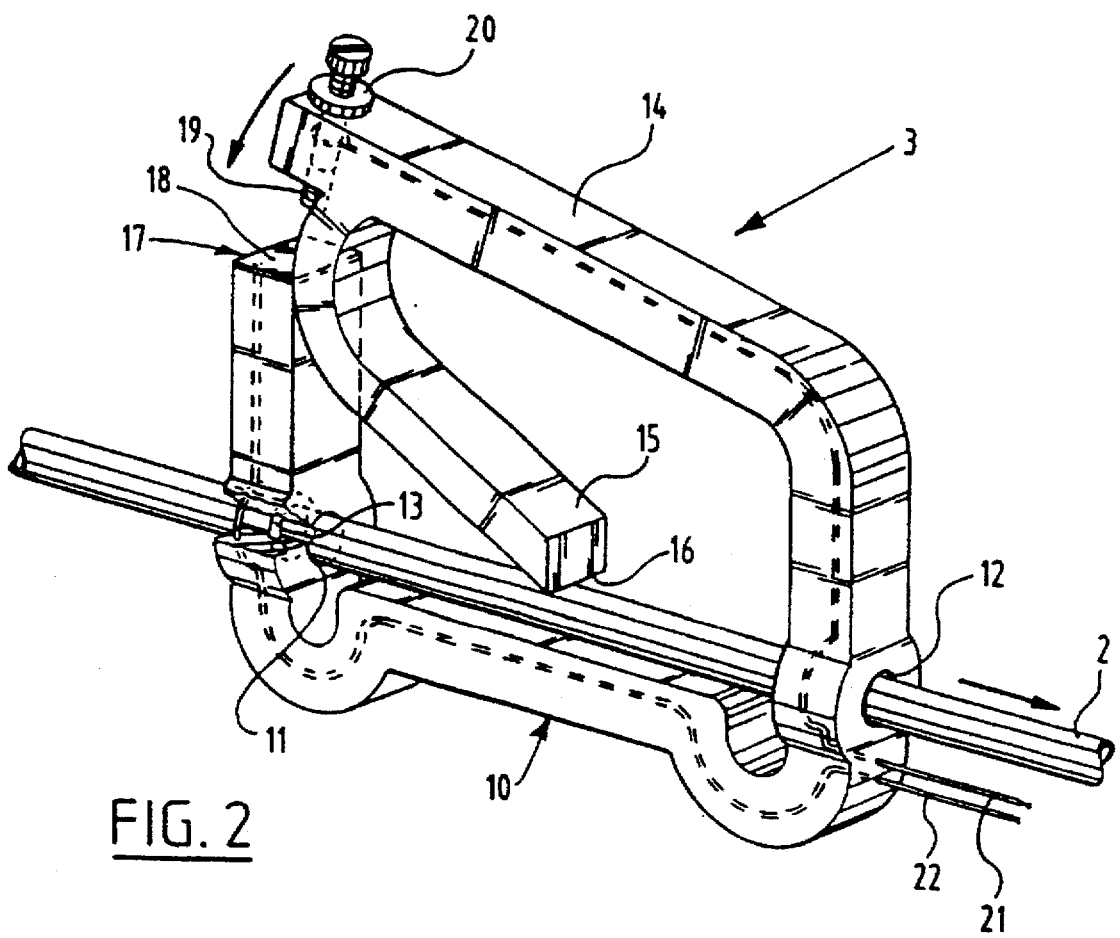
FIGS. 2-7 illustrate six different variants of the embodiment of the device according to the invention.

The device 3 according to the invention illustrated in FIG. 1 is shown in greater detail in FIG. 2. This device 3 comprises a frame 10 in which two guiding openings 11 and 12 have been arranged opposite each other, which form guiding means of the catheter 2. In the guiding opening 11 an o-ring 13, closely fitting around the catheter 2, has been arranged, consequently forming a means of friction for the purpose of generating a frictional force working against he displacement of the catheter.

With the device 3 the catheter 2 can be moved in a controlled manner by pushing the resilient arm 14, forming the first engaging means, down. The second engaging means 15 connected to this arm 14, of which the purpose is to engage the catheter 2, comprises a sharp edge 16 which can engage with the catheter 2. On moving the first engaging means 14 downwards, the sharp edge 16 will move, as seen in FIG. 2, to the right and will consequently move the catheter 2, as a result of this edge 16 engaging with the catheter 2, over a certain distance to the right. On releasing the first engaging means 14 again, the sharp edge 16 will move freely along the body of the catheter 2 back to the left. The catheter 2 is retained in its relative position in relation to the frame 3 by means of the frictional force generated by the o-ring 13.

The distance over which the catheter 2 is moved to the right depends on the distance the first engaging means 14 is moved down. This distance is limited by the stop means 17. This stop means 17 is formed by an adjusting screw 19 which works together with a contact surface 18 of the frame 10. The position of the adjusting screw 19 can be altered by turning it, and the position thus obtained and be fixed by means of the lock nut 20.

An electrical conductor 21 is connected to the adjusting screw 19, and an electrical conductor 22 to the contact surface 18. As soon as the stop means 17 make contact, electrical contact is established between the conductors 21 and 22, which serves as a signal indicating that one displacement stroke of the catheter has been completed.

The entire device 3 has been made of a plastic material and the first engaging means 14, made in the shape of an arm, points upwards, in the position illustrated in FIG. 2, when not in use. Pushing the first engaging means 14 down consequently occurs against a spring force. Operating the device 3 consequently consists of simply compressing the first engaging means 14 and releasing it again. With each stroke the catheter 2 is moved over a certain distance, and every time a signal is given off at the end of each stroke as a result of the adjusting screw 9 and the contact surface 17 coming into contact with each other.

Figure 3:
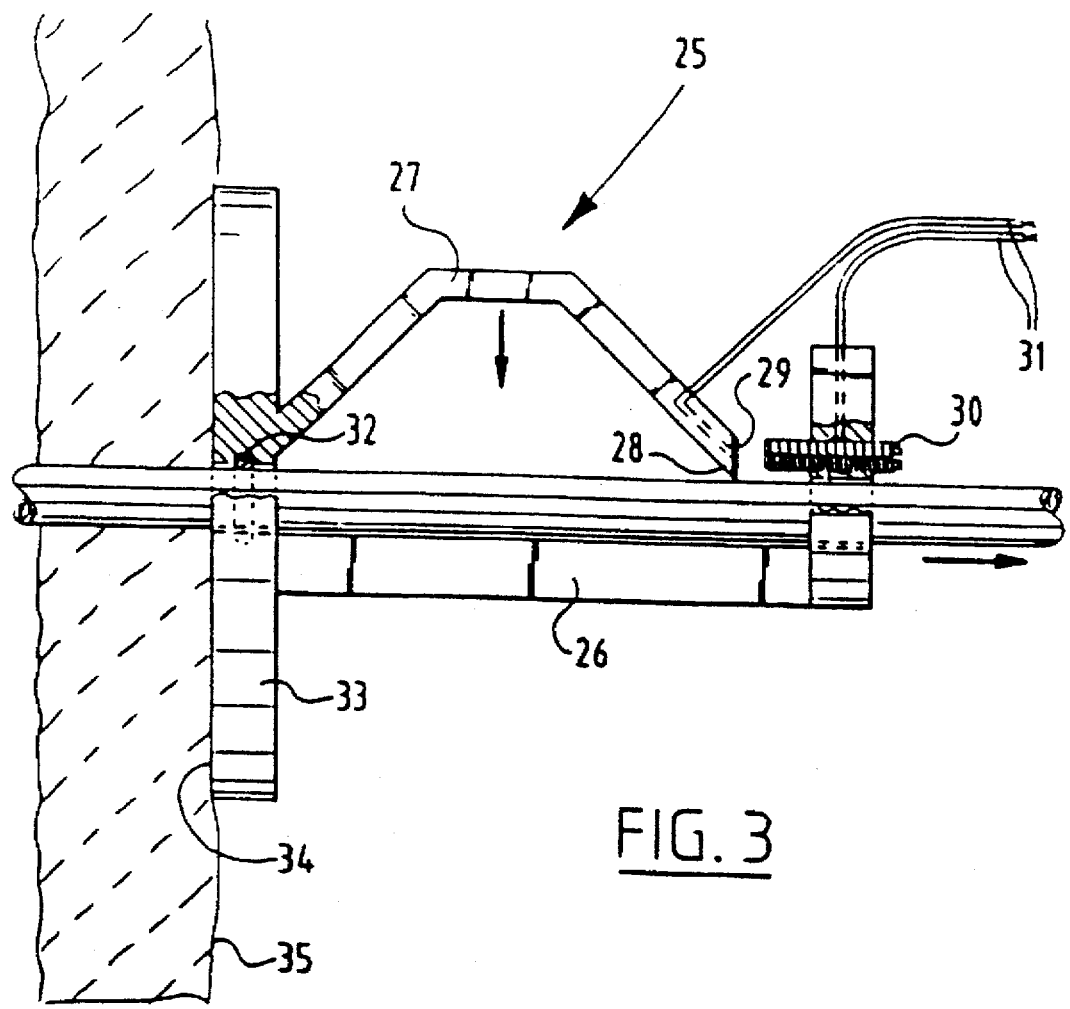

With the device 25 according to the invention illustrated in FIG. 3, the frame 26 is provided with a plate-shaped section 33 which can be attached to the skin 35 of the patient by means of adhesive agents 34 not illustrated in detail here. Consequently, the exact position of the device 25 in relation to the patient can be determined.

The frame 26 of the device 25 is again provided with guiding openings for the catheter. The opening arranged in the plate-section 33 is provided with an o-ring 32 which applies so much friction to the catheter, that it does not move inside the device 26 of its own accord.

The engaging means are formed by the first engaging means 27 which can be operated manually and, connected to it, the second engaging means 28 for the catheter. Once again, the second engaging means 28 comprises a sharp edge, engaging with the catheter.

Directly adjacent to the edge a contact surface 29 has been formed which, as a stop, works together with the adjusting screw 30 arranged in the frame 26; at the same time they form the contact points for the signalling means. The contacts 29 and 30 are led out through conductors 31.

By compressing the first engaging means 27, the second engaging means 28 is moved towards the right as seen in FIG. 3, moving the catheter along. On releasing the first engaging means 27, the sharp edge of the second engaging means 28 moves freely along the catheter to the left whereby the catheter remains fixed in position due to the actin of the o-ring 32. A subsequent stroke can then be carried out by compressing the fist engaging means 27 again. Each time, at the end of each stroke, contact is made between the contact 29 and the adjusting screw 30, so that a signal corresponding to the displacement of the catheter can be conveyed via the conductors 31 to a device connected to them.

Figure 4:
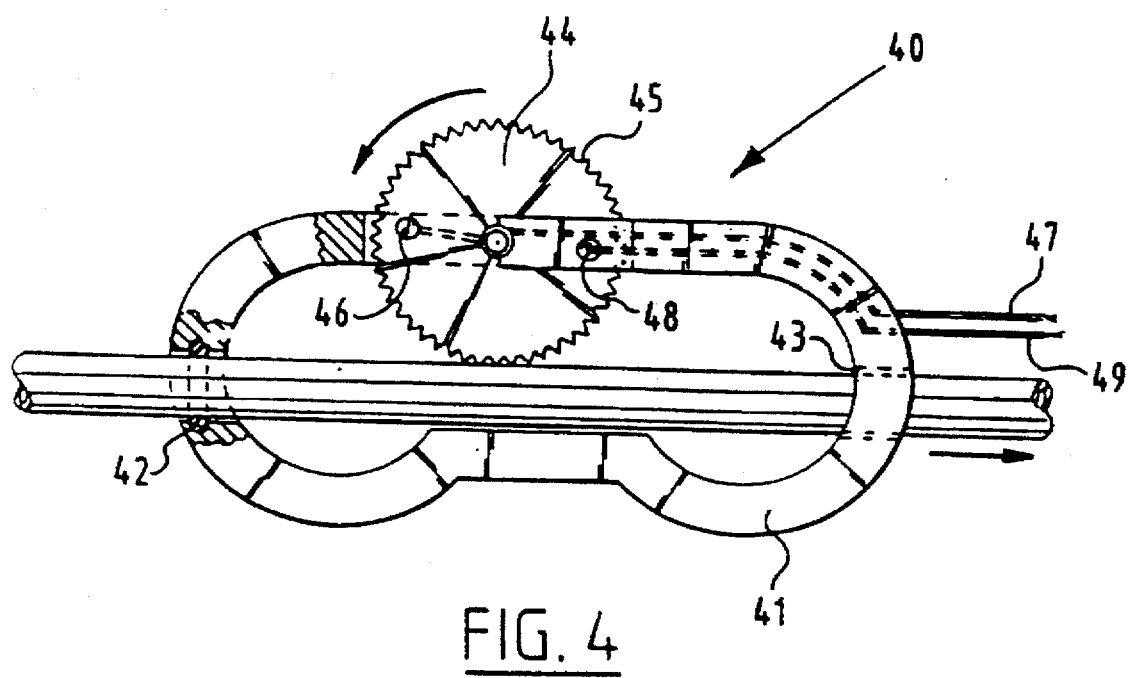

The device 40 of FIG. 4 is not provided with a stepwise but with a more continuous form of activation. Once again, the frame 41 is provided with guiding openings 42 and 43, whereby an o-ring has been received in the guiding opening 42 to provide fixation of the catheter as described above.

The activation is obtained by means of the thumb-wheel 44 which has been provided with a serrated edge 45. The part of the thumb-wheel 44 protruding at the top of the frame 40 forms the first engaging means to be operated by the physician carrying out the procedure using his thumb, whereas the lower part of the thumb-wheel 44 as seen in FIG. 4 with the thumb in the direction of the arrow, the catheter is moved in the direction of the arrow to the right.

In a lateral surface of the thumb-wheel 44 a contact 46 has been formed which can work together with a contact 48 which is connected to a frame 41. The contacts 46 and 48 are connected with for instance the imaging device via conductors 47 and 49 respectively. With each revolution of the thumb-wheel 44 the contacts 46 and 48 will make contact once, so that the displacement of the catheter corresponding to one revolution of the thumbwheel 44 is indicated by a signalling pulse.

With another embodiment part of the edge of the wheel may be free of serrations, allowing intermittent activation.

Figure 5:
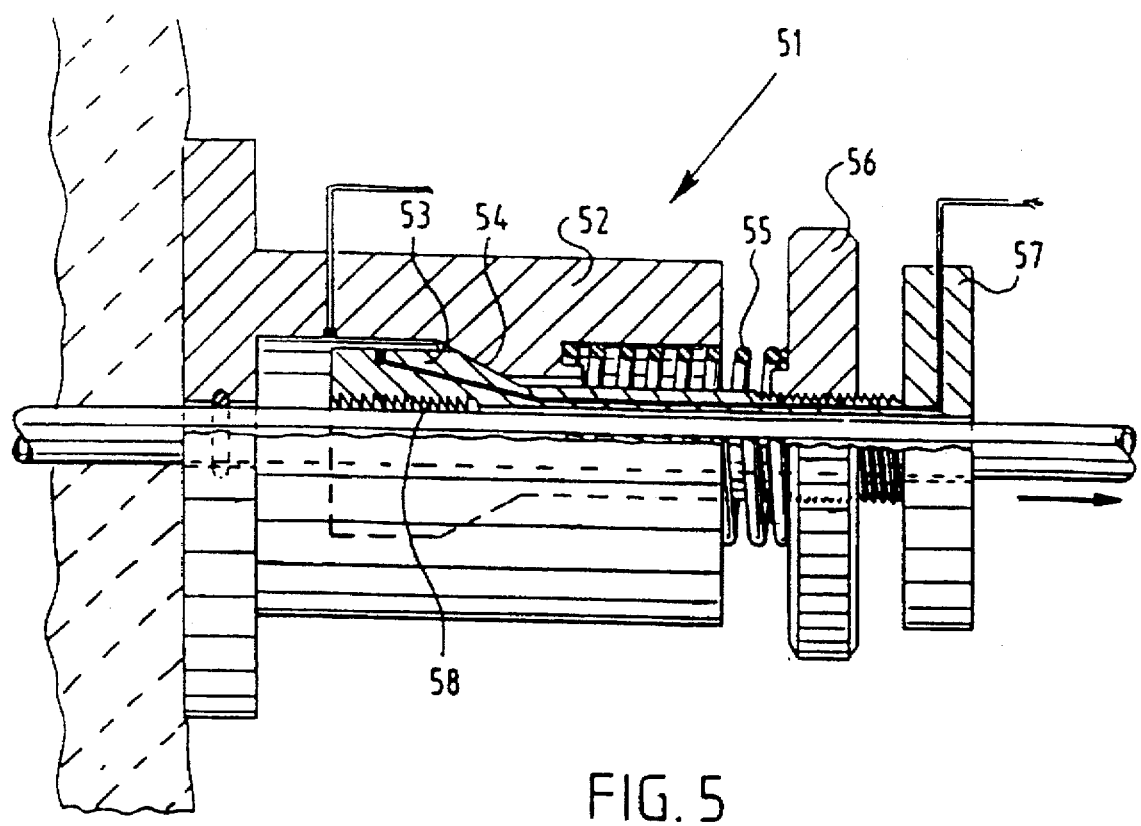

The device 51 of FIG. 5 is once again of the type which is fixed to the skin of a patient by means of adhesive agents. The frame 52 is consequently fixed in relation to the patient. A moveable section 53 has been received in the frame 52 through which the catheter extends. The moveable section 53 protrudes outside the frame 52 with its right end-section as seen in FIG. 5, and supports a pressure piece 57 to which the physician carrying out the procedure can apply pressure with his thumb. On doing so, the pressure piece 57 is moved towards the left, whereby teeth 58 inside the bore through which the catheter extends, move freely along the catheter. The stroke of the pressure piece 57, and consequently that of the moveable section 53, is limited by an adjusting nut 56. The return stroke is caused by a spring 55 which has been arranged around the moveable section 53.

The moveable section 53 and the frame 52 are provided with cone-shaped surfaces 54 working together, which ensure that during the return stroke the teeth 58 engage properly with the catheter in order to pull it along. The action of the device 51 corresponds to that of a "propelled" pencil.

Figure 6:
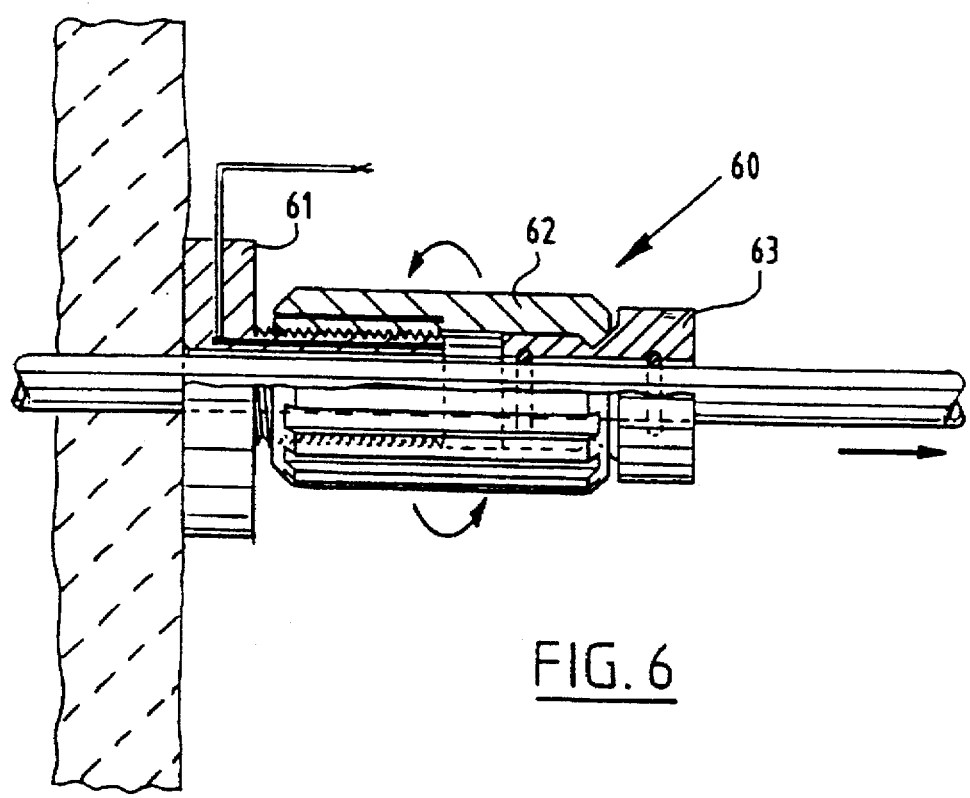

The device 60 of FIG. 6 is a suitable device to withdraw a catheter over a relatively small distance. Also, the device 60 comprises a frame 61 fixed to the skin of the patient, which is consequently relatively immobile. A rotatable section 62 has been screwed on to a threaded section protruding from the right-hand side of the frame 61 which engages in a rotatable manner with a catheter-engaging-section 63. The catheter is fixed into position in this section 63 by o-rings arranged in the section 63. On turning the rotatable piece 62 it moves in a longitudinal direction in relation to the frame 61, and consequently transports the catheter-engaging-section 63 in the same direction. Schematically indicted signalling means can give off a signal at each revolution. The displacement corresponding to each signal is consequently defined by the pitch of the thread. Obviously, it is also possible to employ signalling means which generate a suitable signal a number of times distributed around the circumference.

Figure 7:
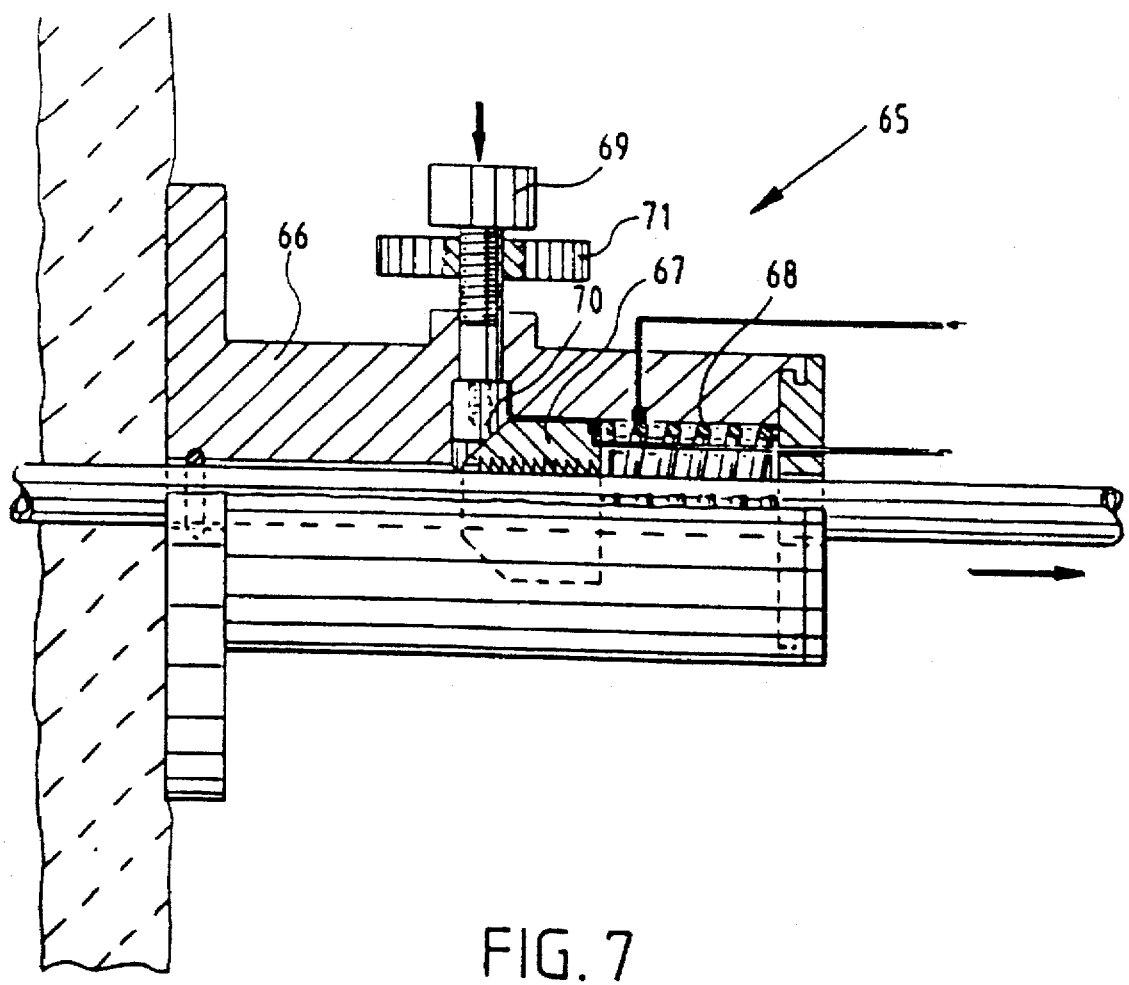

With the device 65 illustrated in FIG. 7, the catheter is once again withdrawn stepwise from the body of the patient by means of a push-button 69. This push-button 69 has been received in a slidable manner in the frame of the device 65 and can be pushed down in a vertical direction. The distance over which the push-button 69 can be moved down is limited by the adjusting nut 71.

The lower end of the push-button 69 is provided with an oblique surface 70, which works together with the oblique surface of a sliding piece 67 received in a slidable manner in the frame 66, which is provided with teeth engaging with the catheter. The sliding piece 67 is pushed towards the left, as seen in FIG. 7, by means of the spring 68.

On pressing the push-button 69, the oblique surface 70 of this push-button pushes the slidable piece 67 to the right, as a result of which the catheter is transported along by the teeth. On releasing the push-button 69 the spring 68 will push the slidable piece 67 to the left, whereby the teeth move freely along the catheter. By pressing the push-button 69 again, the net stroke is effected. Also, in this case suitable signalling means have been arranged, which can give off a signalling pulse for each stroke, every time the push-button 69 is pressed.

By way of adhesive agents adhesives, but also suction cups or similar device may be used. The device may also be attached to the body by means of a clamp around an arm of a leg.

We claim:

1. Device for moving a catheter in a controlled manner, comprising:

a frame;

a guiding means arranged to the frame for the purpose of guiding a catheter;

first engaging means in order to manually engage the guiding means;

second engaging means for the purpose of engaging the catheter guided by said guiding means;

wherein the first and second engaging means are connected in such a manner that, on moving the first engaging means, the catheter is moved in relation to the frame; and electronic signalling means engaged in said first engaging means for the purpose of giving off a signal corresponding to the displacement of the catheter.

2. Device as claimed in claim 1, wherein the first engaging means are moveable to and from in one stroke.

3. Device as claimed in claim 2, further comprising a stop and a body working in conjunction to limit the stroke, and to which contacts which are part of the signalling means are connected.

4. Device as claimed in claim 3, wherein the stop is adjustable.

5. Device as claimed in claim 1, further comprising resilient means which force the first engaging means outwards.

6. Device as claimed in claim 1, wherein the second engaging means engage the catheter in one relative direction of movement and do not engage said catheter in the opposite direction.

7. Device as claimed in claim 1, further comprising frictional means for the purpose of generating a frictional force in the opposite direction of the displacement of the catheter.

8. Device as claimed in claim 7, wherein the frictional means comprise at least one o-ring fitting tightly around the catheter.

9. Device as claimed in claim 1, wherein the frame comprises a plate-like section which is provided with adhesive agents for the purpose of fixing the device to the skin of the patient.

* * * * *